(12) United States Patent
Zhang et al.

(10) Patent No.: US 12,332,231 B2
(45) Date of Patent: Jun. 17, 2025

(54) EXPERIMENTAL DEVICE AND METHOD FOR SOLUBILITY DETERMINATION OF METHANE IN OIL-BASED DRILLING FLUID

(71) Applicant: Southwest Petroleum University, Chengdu (CN)

(72) Inventors: Jie Zhang, Chengdu (CN); Xuefeng Sun, Chengdu (CN); Qiulai Xue, Chengdu (CN); Cuinan Li, Chengdu (CN); Qiang Wei, Chengdu (CN); Zhilin Li, Chengdu (CN); Mubai Duan, Chengdu (CN); Xianjie He, Chengdu (CN)

(73) Assignee: Southwest Petroleum University, Chengdu (CN)

( * ) Notice: Subject to any disclaimer, the term of this patent is extended or adjusted under 35 U.S.C. 154(b) by 235 days.

(21) Appl. No.: 18/346,259

(22) Filed: Jul. 2, 2023

(65) Prior Publication Data

US 2024/0353389 A1    Oct. 24, 2024

(30) Foreign Application Priority Data

Apr. 24, 2023    (CN) .......................... 202310446880.4

(51) Int. Cl.
  *G01N 33/28*    (2006.01)
  *G01N 13/00*    (2006.01)
(52) U.S. Cl.
  CPC ......... *G01N 33/2841* (2013.01); *G01N 13/00* (2013.01); *G01N 33/2823* (2013.01)
(58) Field of Classification Search
  CPC ............... G01N 33/2841; G01N 13/00; G01N 33/2823
  See application file for complete search history.

(56) References Cited

FOREIGN PATENT DOCUMENTS

CN    105806738 A    *    7/2016
CN    106198297 A        12/2016
(Continued)

OTHER PUBLICATIONS

English translation of CN-117471030, accessed from worldwide. espacenet.com.*

(Continued)

*Primary Examiner* — Kristina M Deherrera
*Assistant Examiner* — Jean F Morello
(74) *Attorney, Agent, or Firm* — Nitin Kaushik (57) ABSTRACT

Disclosed is an experimental device and method for solubility determination of methane in oil-based drilling fluid, comprising a pressure-resistant gas chamber and an equilibrium still both arranged in a constant-temperature oil bath heating oven, a gas booster pump, and a vacuum system used for vacuuming the pressure-resistant gas chamber and the equilibrium still, and a data acquisition device for collecting temperature and pressure signals; the gas booster pump is connected to drive air source inlet, a gas check valve is arranged on the pipe between the pressure-resistant gas chamber and the gas booster pump that is also connected with a high-pressure gas cylinder, the equilibrium still is divided into a dissolution equilibrium chamber at the top and a hydraulic oil chamber at the bottom by a high-pressure dynamic seal structure, the dissolution equilibrium chamber is connected to a liquid inlet funnel through the fourth globe valve.

10 Claims, 4 Drawing Sheets

(56) References Cited

FOREIGN PATENT DOCUMENTS

| | | | |
|---|---|---|---|
| CN | 110711548 A | | 1/2020 |
| CN | 111896421 A | | 11/2020 |
| CN | 117471030 A | * | 1/2024 |

OTHER PUBLICATIONS

English translation of CN-105806738, accessed from worldwide.espacenet.com.*

* cited by examiner

EXPERIMENTAL DEVICE AND METHOD FOR SOLUBILITY DETERMINATION OF METHANE IN OIL-BASED DRILLING FLUID

CROSS-REFERENCE TO RELATED APPLICATIONS

The application claims priority to Chinese patent application No. 2023104468804, filed on Apr. 24, 2023, the entire contents of which are incorporated herein by reference.

TECHNICAL FIELD

The invention pertains to the field of extra-deep oil and gas reservoirs drilling in oil and gas exploration and development, in particular to an experimental device and method for solubility determination of methane in oil-based drilling fluid.

BACKGROUND

More efforts have been made in China to promote the drilling and development of extra-deep oil and gas reservoirs achieve increased production, stabilized productivity and enhanced reserves of oil and gas. The high temperature and pressure in deep formation drilling make the methane dissolved in oil-based drilling fluid more easily. The well control staff always overlooks the impact of dissolved gas when dealing with overflow on site. At high temperature and pressure, the increased solubility of methane in drilling fluid will significantly change the rheology and stability of drilling fluid, leading to the risks of gas channeling or overflow on the ground or the drilling fluid column. At 30° C. and 40 MPa, 1 $m^3$ of oil-based drilling fluid dissolves about 3 $m^3$ of methane, and the amount of methane dissolved in oil-based drilling fluid is 100 times that in water-based drilling fluid. Therefore, the prediction of amount of methane dissolved in oil-based drilling fluid at high temperature and pressure makes it easy to explain the mixed migration rule of methane and drilling fluid and the reasons for pressure change in overflow wellbore, with positive significance for the drilling design of extra-deep oil and gas formations and the improvement of decision-making measures for on-site well control treatment. At present, subject to the temperature and pressure range of the experimental system for solubility determination, domestic researchers cannot simulate the actual high temperature and high pressure (HTHP) environment of extra-deep oil and gas reservoirs, so they know little about the solubility of methane in oil-based drilling fluid.

Figure 3:
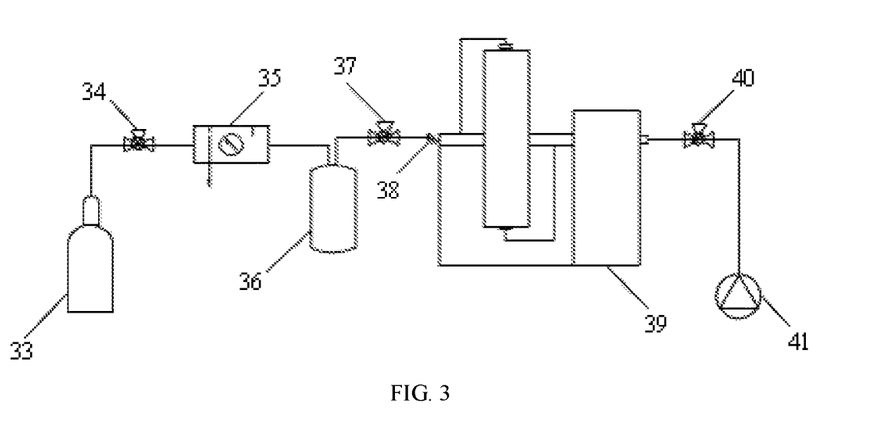
FIG. 3 is a diagram of the existing HTHP dissolution experimental device.
Figure 4:
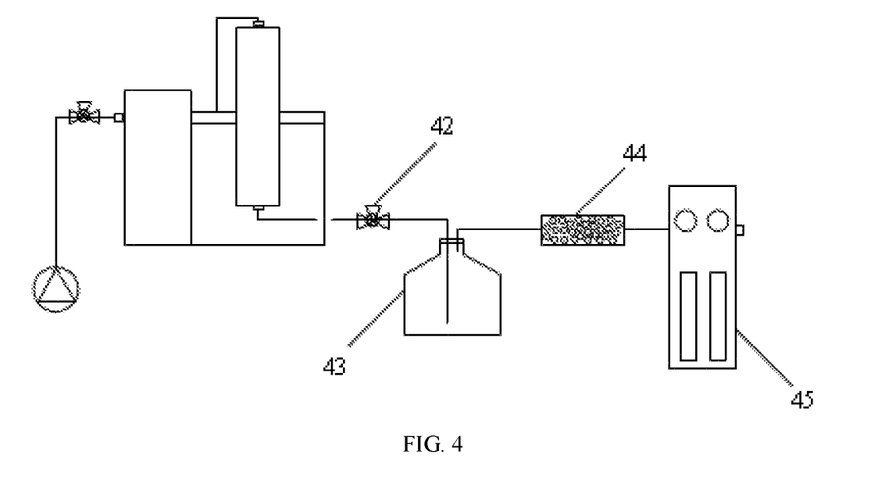
FIG. 4 is a diagram of the existing atmospheric pressure metering experimental device.

At present, the solubility of gas in liquid at high temperature and pressure is determined primarily with the equilibrium liquid sampling method. FIGS. 3 and 4 show the composition and experimental flow of the publicly available device for determining the solubility of methane in drilling fluid by means of equilibrium liquid sampling, including HTHP dissolution experimental system and atmospheric pressure metering experimental system. The HTHP dissolution test system is composed of a gas cylinder (1), a valve I (2), a booster (3), an intermediate vessel (4), a valve II (5), a coil tube (6), a HTHP sample distributor (7), a valve III (8) and a constant pressure pump (9). The atmospheric pressure metering experimental system consists of a constant pressure pump (9) and a HTHP sample distributor (7), which are shared with the HTHP dissolution test system, a valve IV (10), a separation cylinder (11), a dryer (12) and a gas meter (13) which are unique to the atmospheric pressure measurement experimental system. The first step of the method is to transfer the drilling fluid with the measured density into the sample distributor, pressurize the gas in the cylinder, and inject it into the sample distributor, and close the HTHP sample distributor after the specified pressure is reached. The second step is to reach a dissolution equilibrium, specifically control the temperature in the sample distributor by heating the resistor to reach the set temperature, pressurize to the specified value with the constant pressure pump, maintain the dissolution process at a stable pressure, rotate the sample distributor, and accelerate the dissolution reaction, generally reaching dissolution equilibrium in about 3 hours. The third step is to separate and measure, open the valve at the lower end of the sample container, release a small amount of dissolved saturated liquid (3 to 10 ml) to the separation cylinder which is weighed in advance and contains coolant, and flash distill it in the separation cylinder to evolve the gas which flows into the gas volume meter for volume measurement. Finally, calculate the volume of the discharged drilling fluid by the density of drilling fluid and the mass difference before and after flash distillation in the separation cylinder. The ratio of the volume of evolved gas to the volume of the degassed liquid is the solubility at this temperature and pressure.

The existing method has the following disadvantages. 1) After sampling, the original temperature and pressure are changed, the original equilibrium state is destroyed, the solubility results obtained are not consistent, and the sampling may result in gas leakage to damage the samples. 2) Due to the limitations of the determination experiment system, it takes a long time to reach the gas-liquid equilibrium, even taking one day to test one data, and the data often cannot be obtained at high pressure. 3) Different measuring instruments are used for the HTHP gas-liquid dissolution equilibrium and the atmospheric-pressure separation and analysis, respectively, resulting in more measuring devices required, complex device composition, disorderly connections between devices, difficult manufacturing technology, and high cost. 4) The dead volume of space and pipe above the liquid solvent is not included, and the gas-liquid volume is directly recorded without converting the HTHP sample liquid to the standard state (room temperature) during the experimental data processing. 5) It is considered that the liquid is incompressible in the process of pressure boosting, and the volume reduction of the liquid decreases with the increase of the pressure is ignored, especially for the liquid mixed at high pressure, resulting in great error in measurement results.

SUMMARY

In order to solve the problems in the prior art, the invention provides an experimental device and method for solubility determination of methane in oil-based drilling fluid.

The technical solution used in the present invention is:
An experimental device for solubility determination of methane in oil-based drilling fluid comprises a pressure-resistant gas chamber and an equilibrium still both arranged in a constant-temperature oil bath heating oven, a gas booster pump, and a vacuum system used for vacuuming the pressure-resistant gas chamber and the equilibrium still; the gas booster pump is connected to drive air source inlet, a gas check valve is arranged on the pipe between the pressure-resistant gas chamber and the gas booster pump that is also connected with a high-pressure gas cylinder, the equilibrium still is divided into a dissolution equilibrium chamber at the top and a hydraulic oil chamber at the bottom by a high-pressure dynamic seal structure, the dissolution equilibrium chamber is connected to a liquid inlet funnel through the fourth globe valve, and the hydraulic oil chamber is connected to a high-pressure metering pump for replenishing hydraulic oil inside;

A first temperature sensor and a first pressure sensor are provided in the pressure-resistant gas chamber for collecting temperature and pressure signals; a second temperature sensor and a second pressure sensor are provided in the dissolution equilibrium chamber for collecting temperature and pressure signals; the first temperature sensor, the first pressure sensor, the second temperature sensor, and the second pressure sensor are connected to the data acquisition device.

Further, a gas filter, a first relief valve, a second pressure gauge and an electric valve are installed on the pipe between the air source inlet and the gas booster pump.

Further, the experimental device further comprises a first pressure gauge for measuring the pressure of the high-pressure gas cylinder and a first globe valve for controlling its switch.

Further, the pipe between the pressure gas chamber and the gas booster pump is also provided with a second relief valve and a second globe valve.

Further, an agitator blade for agitation is set inside the dissolution equilibrium chamber, and is connected with an agitator motor.

Further, the vacuum system is composed of a vacuum pump, with a fifth globe valve set between the vacuum pump and the equilibrium still, and a third globe valve set between the pressure-resistant gas chamber and the equilibrium still.

Further, the data acquisition device is connected to a controller.

A method using the experimental device for solubility determination of methane in oil-based drilling fluid, comprising the following steps:

Step 1: Calibrate and verify the experimental device and pipe;

Step 2: Clean the equilibrium still, turn on the vacuum system to vacuum, and test the air tightness of the experimental device;

Step 3: Heat the pressure-resistant gas chamber and the equilibrium still to the target temperature, turn on the vacuum system for vacuuming, and inject the required drilling fluid into the dissolution equilibrium chamber in the equilibrium still through the feed funnel;

Step 4: Fill a certain amount of methane into the pressure-resistant gas chamber, heat the pressure-resistant gas chamber to the target temperature, and obtain the temperature $T_1$ and pressure $P_1$ of the methane in the pressure-resistant gas chamber after the pressure is stabilized;

Step 5: Inject methane from the pressure-resistant gas chamber into the dissolution equilibrium chamber of the equilibrium still until it reaches the set pressure, and obtain the temperature $T_2$ and pressure $P_2$ as the gas is released from the pressure-resistant gas chamber after the pressure is stabilized;

Step 6: Adjust the constant-temperature oil bath heating oven to reach the required temperature, and observe the pressure change in the dissolution equilibrium chamber in real time. If the pressure decreases, inject hydraulic oil into the hydraulic oil chamber through the high-pressure metering pump until reaching the set pressure, and record $T_3$ and $P_3$ in the equilibrium still after the pressure is stabilized;

Step 7: Calculate the solubility of methane in oil-based drilling fluid based on the measured parameters.

Further, the solubility $R_S$ of methane in oil-based drilling fluid is calculated as follows:

$$n = \Delta n_g - n_{g3} = (n_{g1} - n_{g2}) - n_{g3}$$

Where, n is the mole fraction of methane dissolved in the oil-based drilling fluid; $n_{g3}$ is the mole number of methane in the equilibrium still after the dissolution equilibrium is reached; $\Delta n_g$ is the mole number of methane released from the pressure-resistant gas chamber into the equilibrium still; $n_{g1}$ is the mole number of methane in the pressure-resistant gas chamber before it is released into the equilibrium still; $n_{g2}$ is the mole number of methane in the pressure-resistant gas chamber after it is released into the equilibrium still;

The solubility $R_S$ is:

$$R_S = (n \times 22.4 \times 10^3)/V_L$$

Where, $V_L$ is the volume of oil-based drilling fluid at room temperature and atmospheric pressure.

Further, the method also comprises the correction of the mole fraction n of methane dissolved in oil-based drilling fluid as follows:

Step 1: Convert the mole fraction n of methane dissolved in oil-based drilling fluid is to the following formula:

$$n = \frac{V_{GC}(\rho_i - \rho_f)}{M_g} - (V_{EC} - V_L)\frac{\rho_g}{M_g} \quad (1)$$

Where, $V_{GC}$ is the volume of pressure-resistant gas chamber (15); $V_{EC}$ is the volume of equilibrium still (25); $V_L$ is the volume of oil-based drilling fluid added into the equilibrium still (25); $\rho_i$ is the density of methane in the pressure-resistant gas chamber (15) before it is released into the equilibrium still (25); $\rho_f$ is the density of methane in the pressure-resistant gas chamber (15) after it is released into the equilibrium still (25); $\rho_g$ is the molar density of methane in the equilibrium still after reaching dissolution equilibrium; $M_g$ is the molar mass of methane;

Step 2: Correct the influence of temperature and pressure on drilling fluid density;

$$\rho_2 = \rho_1/(1 + C_T \Delta T + C_P \Delta P) \quad (2)$$

Where, $\rho_1$ is the density of drilling fluid at room temperature and atmospheric pressure; $C_T$ is the coefficient of thermal expansion; $C_P$ is the coefficient of elastic compression; $\Delta T$ is the temperature difference between the measured target temperature and room temperature; $\Delta P$ is the pressure difference between the measured target pressure and atmospheric pressure;

Step 3: Correct the impact of temperature and pressure on the change of drilling fluid volume;

$$\Delta V = -\frac{\Delta \rho}{\rho}V_L = -\frac{\rho_2 - \rho_1}{\rho_1}V_L \quad (3)$$

Where, $\rho_2$ is the density of drilling fluid at the measured target temperature and pressure; $\rho_1$ is the density of drilling fluid at room temperature and atmospheric pressure; $V_L$ is the volume of oil-based drilling fluid at room temperature and atmospheric pressure; and $\Delta V$ is the volume change of drilling fluid caused by temperature and pressure changes;

Step 4: Correct the mole number n of methane dissolved in oil-based drilling fluid under high temperature and high pressure;

$$n = \frac{(V_{GC} + V_{pipe})(\rho_i - \rho_f)}{M_g} - [V_{EC} - (V_L + \Delta V) - V_{pump}]\frac{\rho_g}{M_g} \quad (4)$$

Where, $V_{pump}$ is the volume change caused by the filled hydraulic oil in the high-pressure metering pump (23), and $V_{pipe}$ is the volume occupied by the valve.

The present invention has the following beneficial effects.

(1) The pressure-resistant gas chamber (15) and the equilibrium still (25), used in the invention to measure the solubility of methane in oil-based drilling fluid at high temperature and pressure, can simulate the HTHP environment of the extra-deep oil and gas reservoirs with overflow gas and drilling fluid. They are relatively simple in operation, technologically advanced, and reasonably designed in structure, with such characteristics as high temperature resistance, high pressure resistance, good sealing effect, compact size, light weight, and beautiful and generous appearance.

(2) All pressure-bearing parts of the gas pressurization system adopted in the invention are standard as stipulated in the specification, and easy to be disassembled, with high safety factor, long service life, and convenient maintenance.

(3) An equal volume saturation method is adopted in the invention, without dynamic sampling which may destroy the saturated liquid composition of the equilibrium system, thereby improving the experimental efficiency.

(4) The invention provides a determination and data processing method with high reliability, which can calculate the solubility of methane in oil-based drilling fluid according to the corrected pressure and volume data, so as to improve the reliability of solubility determination data. The obtained solubility results are closer to practical engineering applications, thus providing scientific data support for the exploration and development of extra-deep oil and gas reservoirs.

Explanation of numbers marked in the figure: 1—High-pressure gas cylinder, 2—First pressure gauge, 3—First globe valve, 4—Booster pump, 5—Drive air source inlet, 6—Gas filter, 7—First relief valve, 8—Second pressure gauge, 9—Electric valve, 10—Gas check valve, 11—Second relief valve, 12—Second globe valve, 13—First temperature sensor, 14—First pressure sensor, 15—Pressure-resistant gas chamber, 16—Third globe valve, 17—Second temperature sensor, 18—Agitator motor, 19—Agitator blade, 20—High-pressure dynamic seal structure, 21—Liquid inlet funnel, 22—Fourth globe valve, 23—High-pressure metering pump, 24—Second pressure sensor, 25—Equilibrium still, 26—Constant-temperature oil bath heating oven, 27—Hydraulic oil chamber, 28—Fifth globe valve, 29—Vacuum pump, 30—Vacuum system, 31—Data acquisition device, 32—Controller;

33—Gas cylinder, 34—Valve I, 35—Booster, 36—Intermediate vessel, 37—Valve II, 38—Coil tube, 39—High temperature and high pressure dispenser, 40—Valve III, 41—Constant pressure pump, 42—Valve IV, 43—Separation bottle, 44—Dryer, 45—Gas gauge.

DETAILED DESCRIPTION OF THE EMBODIMENTS

The present invention is further described with reference to the drawings and embodiments.

Figure 1:
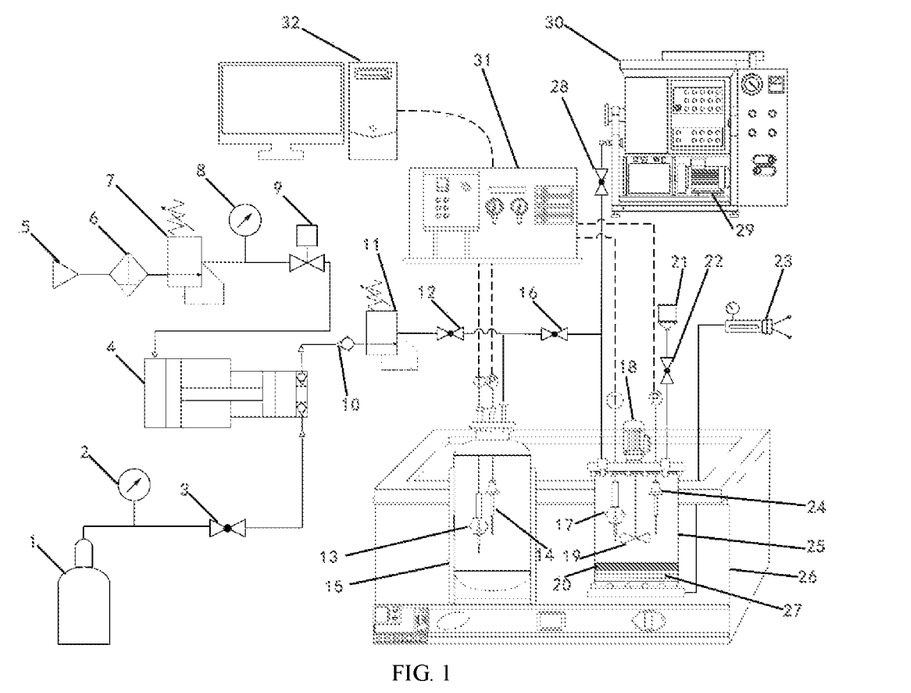
FIG. 1 is a schematic structural diagram of the experimental device of the present invention.

As shown in FIG. 1, an experimental device for solubility determination of methane in oil-based drilling fluid comprises a pressure-resistant gas chamber (15) and an equilibrium still (25) both arranged in a constant-temperature oil bath heating oven (26), a gas booster pump (4), and a vacuum system (30) used for vacuuming the pressure-resistant gas chamber (15) and the equilibrium still (25), wherein the gas booster pump (4) is connected to drive air source inlet (5), a gas check valve (10) is arranged on the pipe between the pressure-resistant gas chamber (15) and the gas booster pump (4) that is also connected with a high-pressure gas cylinder (1), the equilibrium still (25) is divided into a dissolution equilibrium chamber at the top and a hydraulic oil chamber (27) at the bottom by a high-pressure dynamic seal structure (20), the dissolution equilibrium chamber is connected to a liquid inlet funnel (21) through the fourth globe valve (22), the hydraulic oil chamber (27) is connected to a high-pressure metering pump (23) for replenishing hydraulic oil inside, and the high-pressure metering pump (23) is a hand high-pressure metering pump.

The constant-temperature oil bath heating oven (26) is intelligently controlled and automatically adjusted for its temperature. A gas filter (6), a first relief valve (7), a second pressure gauge (8) and an electric valve (9) are installed on the pipe between the air source inlet (5) and the gas booster pump (4). After the electric valve (9) is opened, the air passes through the gas filter (6) and the first relief valve (7), serving as the driving air source of the booster pump (4), and is discharged by the high-pressure piston that is continuously controlled by the gas check valve (10) in the pump. The methane in the high-pressure cylinder (1) is pressurized to the target experimental pressure and injected into the pressure-resistant gas chamber (15).

The experimental device for solubility determination also includes a first pressure gauge (2) for measuring the pressure of the high-pressure gas cylinder (1) and a first globe valve (3) for controlling its switch. The pipe between the pressure gas chamber (15) and the gas booster pump (4) is also provided with a second relief valve (11) and a second globe valve (16). An agitator blade (19) for agitation is set inside the dissolution equilibrium chamber, and is connected with an agitator motor (18) which can accelerate the dissolution of methane in oil-based drilling fluid. The vacuum system (30) is composed of a vacuum pump (29), with a fifth globe valve (28) set between the vacuum pump (29) and the equilibrium still (25), and a third globe valve (16) set between the pressure-resistant gas chamber (15) and the equilibrium still (25). After the third globe valve (16) is opened, the methane in the pressure-resistant gas chamber (15) is released into the equilibrium still (25), so as to sample an accurate amount of methane in the pressure-resistant gas chamber (15).

A first temperature sensor (13) and a first pressure sensor (14) are provided in the pressure-resistant gas chamber (15) for collecting temperature and pressure signals; a second temperature sensor (17) and a second pressure sensor (24) are provided in the dissolution equilibrium chamber for collecting temperature and pressure signals; the first temperature sensor (13), the first pressure sensor (14), the second temperature sensor (17), and the second pressure sensor (24) are connected to the data acquisition device (31).

The data acquisition device (31) is connected to a controller (32) which can be a computer. The output signals from the temperature sensor and the pressure sensor are processed and converted into digital signals by the data acquisition device (31), which are displayed on the computer.

Figure 2:
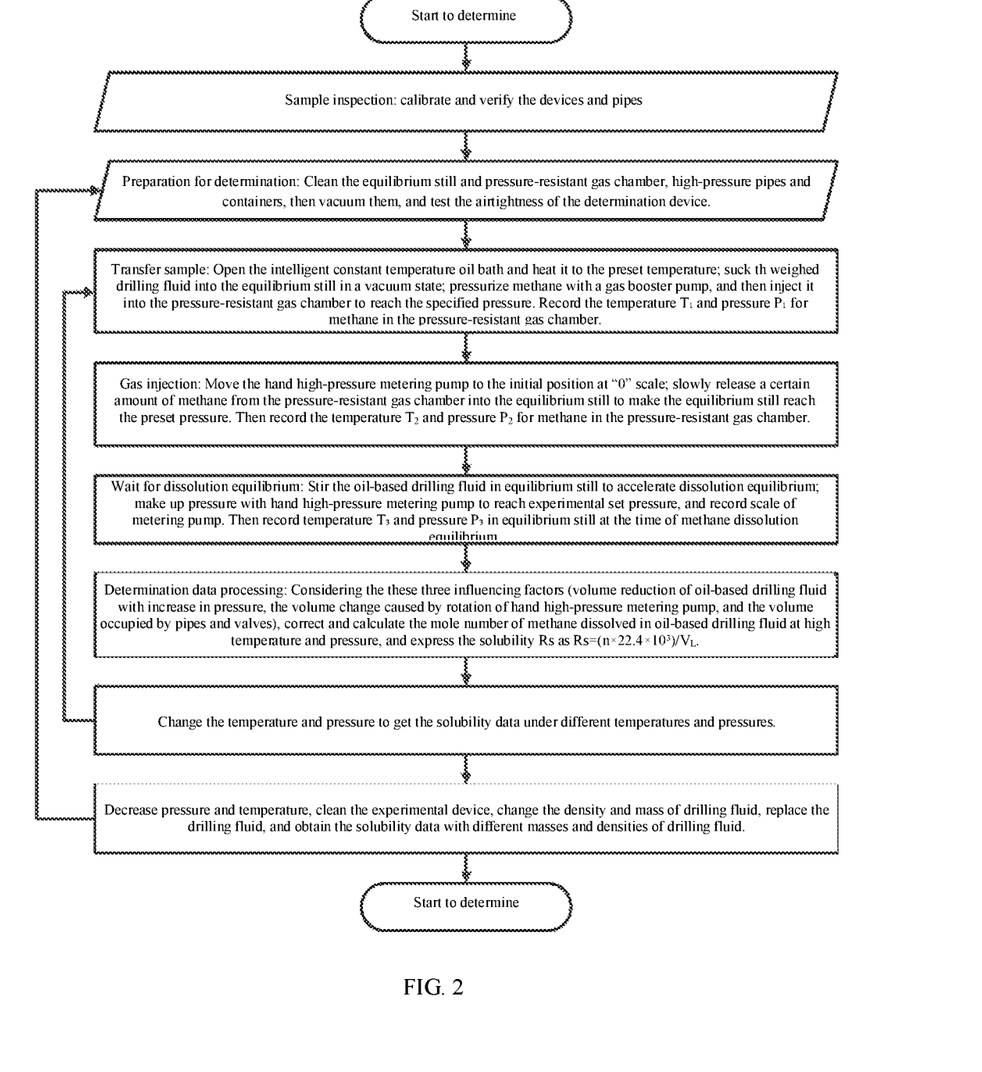
FIG. 2 is a flow diagram of the determination method of the invention.

As shown in FIG. 2, a method for solubility determination of methane in oil-based drilling fluid comprises the following steps.

Before the experiment, the sample should be checked first. When receiving the samples, check whether the quantity and label information of the samples are consistent with the sample delivery sheet, and check the appearance of sample container for leakage and other defaults.

Step 1: Calibrate and verify the experimental device and pipe;

Volume calibration: Calibrate the volume respectively of the pressure-resistant gas chamber (15) and the equilibrium still (25) by filling them with liquid water at room temperature and atmospheric pressure prior to methane solubility determination. Specific calibration consists of the following steps. Firstly, weigh the mass of the filled water with an electronic analytical balance, measure the room temperature and atmospheric pressure, and then work out the density of the water at such room temperature and atmospheric pressure with the software REFPROP. After calibration, the volumes of pressure-resistant gas chamber (15) and equilibrium still (25) are consistent with the factory parameters, 500 ml and 400 ml, respectively.

Calibration of pipe valve volume: Open the first globe valve (3) and the second globe valve (12), and inject a certain pressure of gas into the pressure-resistant gas chamber (15); close the first globe valve (3) and the second globe valve (12), stabilize fora period of time, and record the pressure and temperature of the pressure-resistant gas chamber (15) at this time. Then open the third globe valve (16), release the gas in the pressure-resistant gas chamber (15) into the equilibrium still (25), close the third globe valve (16), stabilize for 30 minutes, record the temperature and pressure in the equilibrium still (25), and calculate that the volume of the pipe and valve is 28.61 cm$^3$.

Step 2: Clean the equilibrium still (25), turn on the vacuum system (30) to vacuum, and test the air tightness of the experimental device;

Connect the determination experimental device in advance. First, add petroleum ether into the equilibrium still (25), stir for 1 hour, blow air into the equilibrium still (25) to blow out the petroleum ether and other impurities, and repeat cleaning 2 to 3 times to ensure that the still is clean.

In order to ensure the accuracy of the pressure measurement, first vacuum the device to the ultimate vacuum pressure with the vacuum system (30), then inject methane into the device, vacuum again and repeat 2 to 3 times to make the device reach the ultimate vacuum.

After vacuuming the whole device, close the fifth globe valve (28) and check whether the device can maintain vacuum to determine whether there is leakage in the experimental device. If no leakage, open the high-pressure gas cylinder (1), pump methane into the pressure-resistant gas chamber (16) and the equilibrium still (25) with the gas booster pump (4) to make the pressure reach about 30 MPa, and then observe whether the pressure is changed in the pressure-resistant gas chamber (15) and the equilibrium still (25) after an hour. If the pressure change of the experimental device is higher than 0.02 MPa, it indicates that the device is not sealed, and then the joints are checked with leakage test solution until there is no leakage.

Step 3: Heat the pressure-resistant gas chamber (15) and the equilibrium still (25) to the target temperature, turn on the vacuum system (30) for vacuuming, and inject the required drilling fluid into the dissolution equilibrium chamber in the equilibrium still (25) through the feed funnel (21).

The specific process is as follows:

The process of transferring liquid samples is as follows: Evacuate the equilibrium still (25) and external pipes to 133 Pa and continually evacuate for 30 minutes to vacuum the entire device; transfer a certain amount of drilling fluid weighed by the electronic analytical balance to the feed hopper (21), and then suck it into the equilibrium still (25) through the fourth globe valve (22).

Step 4: Fill a certain amount of methane into the pressure-resistant gas chamber (15), heat the pressure-resistant gas chamber (15) to the target temperature, and obtain the temperature $T_1$ and pressure $P_1$ of the methane in the pressure-resistant gas chamber (15) after the pressure is stabilized.

The process of transferring gas samples is as follows: Open the first globe valve (3) and the second globe valve (12), close the third globe valve (16), fill a certain amount of methane into the pressure-resistant gas chamber (15), adjust the constant-temperature oil bath heating oven (26) to reach the experimental target temperature, and record the temperature $T_1$ and pressure $P_1$ of methane in the pressure-resistant gas chamber (15) after the pressure is stabilized. The maximum working pressure of the high-pressure cylinder (1) is 13.5 MPa. If the pressure of high pressure cylinder (1) is lower than the pressure to be measured, the gas pressure should be boosted by the gas booster pump (4).

Step 5: Inject methane from the pressure-resistant gas chamber (15) into the dissolution equilibrium chamber of the equilibrium still (25) until it reaches the set pressure, and obtain the temperature $T_2$ and pressure $P_2$ as the gas is released from the pressure-resistant gas chamber (15) after the pressure is stabilized.

At room temperature and atmospheric pressure, move the hand high-pressure metering pump (23) to the initial position at "0" scale, and screw in the scale of the hand high-pressure metering pump by 1 ml, that is, the volume of the equilibrium still (25) is reduced by 1 ml. Open the third globe valve (16), close the second globe valve (12), slowly inject a certain amount of methane from the pressure-resistant gas chamber (15) into the equilibrium still (25) to reach the set pressure in the equilibrium still (25), close the third globe valve (16), and after the pressure is stabilized, record the temperature $T_2$ and pressure $P_2$ as the gas is released from the pressure-resistant gas chamber (15) after the pressure is stabilized.

Step 6: Adjust the constant-temperature oil bath heating oven (26) to reach the required temperature, and observe the pressure change in the dissolution equilibrium chamber in real time. If the pressure decreases, inject hydraulic oil into the hydraulic oil chamber (27) through the high-pressure metering pump (23) until reaching the set pressure, and record $T_3$ and $P_3$ in the equilibrium still (25) after the pressure is stabilized.

Adjust the constant-temperature oil bath heating oven (26) to make the temperature reach the value set by the experiment, and keep the temperature stable. At the same time, turn on the agitator motor (18) to drive the agitator blade (19) to stir the oil-based drilling fluid in the equilibrium still (25), and then accelerate the dissolution rate of measured methane in the oil-based drilling fluid, and shorten the time to reach the dissolution equilibrium. As the methane dissolves into the oil-based drilling fluid, the pressure in the equilibrium still (25) decreases at this fixed temperature. At this time, slow push the hydraulic oil into the equilibrium still (25) to the hydraulic oil chamber (27) with the high-pressure metering pump (23), make up the pressure to the set pressure of the experiment, and record the scale of the high-pressure metering pump (23). Usually, stir the oil-based drilling fluid inside the equilibrium still (25) or about 1 hour while observing the pressure of the equilibrium still (25). If it decreases, make up the pressure with the metering pump (23), and record the scale of the pump again. When the system pressure in the equilibrium still (25) is stable and constant to reach an equilibrium, turn off the agitator motor (18) and record the temperature $T_3$ and pressure $P_3$ in the equilibrium still at the time of methane dissolution equilibrium.

Step 7: Calculate the solubility of methane in oil-based drilling fluid based on the measured parameters.

The solubility $R_S$ of methane in oil-based drilling fluid is calculated as follows:

$$n = \Delta n_g - n_{g3} = (n_{g1} - n_{g2}) - n_{g3}$$

Where, n is the mole fraction of methane dissolved in the oil-based drilling fluid; $n_{g3}$ is the mole number of methane in the equilibrium still (25) after the dissolution equilibrium is reached, in mol; $\Delta n_g$ is the mole number of methane released from the pressure-resistant gas chamber (15) into the equilibrium still (25), in mol; $n_{g1}$ is the mole number of methane in the pressure-resistant gas chamber (15) before it is released into the equilibrium still (25), in mol; $n_{g2}$ is the mole number of methane in the pressure-resistant gas chamber (15) after it is released into the equilibrium still (25), in mol.

Since the volume of the pressure-resistant gas chamber (15), the temperature $T_1$ and the pressure $P_1$ of the methane are known, the mole number $n_{g1}$ of methane in the pressure-resistant gas chamber (15) can be calculated before methane is released to the equilibrium still (25). The $T_2$ and pressure $P_2$ of methane in the pressure-resistant gas chamber (15) recorded after methane is released into the equilibrium still (25) are recorded, and the PVT data of methane are known, the mole number $n_{g2}$ of methane remaining in pressure-resistant gas chamber (15) methane is released can be determined. Taking into account the volume change caused by the rotation of the high-pressure metering pump (23) and the volume occupied by pipes and valves, the volume $V_L$ of oil-based drilling fluid is easily worked out based on the known mass and density of the oil-based drilling fluid added, so as to correct the volume of methane in the equilibrium still (25) when dissolution equilibrium is reached in oil-based drilling fluid. Moreover, the temperature $T_3$ and pressure $P_3$ in the equilibrium still (25) at the time of dissolution equilibrium are known, so the mole number $n_{g3}$ of the gas in the equilibrium still can be determined after the dissolution equilibrium is reached.

The solubility $R_S$ is:

$$R_S = (n \times 22.4 \times 10^3)/V_L$$

Where, $V_L$ is the volume of oil-based drilling fluid at room temperature and atmospheric pressure.

The mole fraction n of methane dissolved in oil-based drilling fluid is corrected as follows:

Step 1: Convert the mole fraction n of methane dissolved in oil-based drilling fluid is to the following formula:

$$n = \frac{V_{GC}(\rho_i - \rho_f)}{M_g} - (V_{EC} - V_L)\frac{\rho_g}{M_g} \quad (1)$$

Where, $V_{GC}$ is the volume of pressure-resistant gas chamber (15), in ml; $V_{EC}$ is the volume of equilibrium still (25), in ml; $V_L$ is the volume of oil-based drilling fluid added into the equilibrium still (25), in ml; $\rho_i$ is the density of methane in the pressure-resistant gas chamber (15) before it is released into the equilibrium still (25), in g/cm$^3$; $\rho_f$ is the density of methane in the pressure-resistant gas chamber (15) after it is released into the equilibrium still (25), in g/cm$^3$; $\rho_g$ is the molar density of methane in the equilibrium still after reaching dissolution equilibrium, in g/cm$^3$; $M_g$ is the molar mass of methane, in 16 g/mol. $\rho_i$, $\rho_f$ and $\rho_g$ are obtained from the database of the software REFPROP 9.1.

Step 2: Correct the influence of temperature and pressure on drilling fluid density;

$$\rho_2 = \rho_1/(1 + C_T\Delta T + C_P\Delta P) \quad (2)$$

Where, $\rho_1$ is the density of drilling fluid at room temperature and atmospheric pressure, in g/cm$^3$; $C_T$ is the coefficient of thermal expansion, in MPa; $C_p$ is the coefficient of elastic compression, in MPa; $\Delta T$ is the temperature difference between the measured target temperature and room temperature, in °C.; $\Delta P$ is the pressure difference between the measured target pressure and atmospheric pressure, in MPa.

$$C_T = b\rho_1/(1 + a\Delta P), C_p = k\rho_1\Delta P^n, \Delta T = T - T_o, \Delta P = P - P_o$$

Where, $T_0$ is room temperature, in °C.; $p_o$ is atmospheric pressure, in MPa; T is the target temperature, in °C.; P is the target pressure, in MPa; a, b, k and n are calculated empirical values.

Step 3: Correct the impact of temperature and pressure on the change of drilling fluid volume; the volume or density of drilling fluid will vary with the pressure it is subjected to, that is, when the pressure increases by one unit value, the volume of the drilling fluid decreases by one relative value. As the pressure increases, the volume decreases, but the mass remains unchanged, that is, dm=0, so the density increases. The relationship between the relative increments can be determined by dm=d (ρV)=ρdV+Vdρ=0:

$$\Delta V = -\frac{\Delta \rho}{\rho} V_L = -\frac{\rho_2 - \rho_1}{\rho_1} V_L \quad (3)$$

Where, $\rho_2$ is the density of drilling fluid at the measured target temperature and pressure, in g/cm³; $\rho_1$ is the density of drilling fluid at room temperature and atmospheric pressure, in g/cm³; $V_L$ is the volume of oil-based drilling fluid at room temperature and atmospheric pressure, in cm³; and $\Delta V$ is the volume change of drilling fluid caused by temperature and pressure changes, in cm³.

Step 4: Correct the mole number n of methane dissolved in oil-based drilling fluid under high temperature and high pressure: consider three influencing factors (the volume reduction $\Delta V$ of oil-based drilling fluid with increase in pressure, the volume change $V_{pump}$ caused by rotation of high-pressure metering pump (23), and the volume $V_{pipe}$ occupied by pipes and valves), and combine the formulas (1) to (3) to obtain:

$$n = \frac{(V_{GC} + V_{pipe})(\rho_i - \rho_f)}{M_g} - [V_{EC} - (V_L + \Delta V) - V_{pump}]\frac{\rho_g}{M_g} \quad (4)$$

Where, $V_{pump}$ is the volume change caused by the filled hydraulic oil in the high-pressure metering pump (23), and $V_{pipe}$ is the volume occupied by the valve.

In the invention, the HTHP equilibrium still (25) is made of 316L stainless steel, used to contain the mixture of gas solute and drilling fluid, and opened or closed with high-pressure flange bolts; the seal structure is comprised of O metal seal ring and metal corrugated gasket. The equilibrium still (25) can actualize automatic relief in case of overpressure, with a maximum operating temperature of 200° C., a maximum operating pressure of 75 MPa, and a volume of 400 ml. With excellent resistance against corrosion, high temperature and high pressure, it can simulate the HTHP conditions in the actual ultra-deep oil and gas drilling process, making it easier to understand the production conditions, obtain accurate experimental data, and prevent against leakage problems caused by long-term use, high temperature and high pressure, greatly improving the safety and stability of experimental operations. The pressure-resistant gas chamber (15), made of 316 L stainless steel, is a container of gas solutes, with a maximum operating temperature of 200° C., a maximum pressure capacity of 150 MPa, and a volume of 500 ml. It can strictly control the amount of methane released into the equilibrium still (25), thus sampling an accurate amount of methane in the pressure-resistant gas chamber (15).

The agitator motor (18) is a adjustable-speed automatic motor that is integrated with the top cover of the equilibrium still (25), and used to drive the agitator blade (19) inside the still, with an explosion protection of BT4, low noise and smooth speed regulation, accelerating the dissolution rate of the determined methane in the oil-based drilling fluid, shortening the determined time to reach a dissolution equilibrium, and greatly improving the experimental efficiency.

A high-precision dynamic seal structure (20) is arranged inside the equilibrium still (25) to divide the space of the equilibrium still (25) into a dissolution equilibrium chamber located above the seal structure (20) and a hydraulic oil chamber (27) located below the seal structure (20) and connected to the high-pressure metering pump (23) through the pipe from the bottom cover of the equilibrium still (25). With an operating range of 310 ml, a minimum scale resolution of 0.01 ml, and a rated maximum operating pressure of 75 MPa, the high-pressure metering pump (23) is used to keep the pressure in the equilibrium still (25) to be constant as the predetermined target experimental pressure, because the pressure in the HTHP reaction still (equilibrium still) (25) will decrease when dissolution equilibrium is reached. The hydraulic oil at the bottom of the pressurized equilibrium still (25) is pushed by the hand crank of the high-pressure metering pump (23) to supplement the pressure that decreases due to methane dissolution in the oil-based drilling fluid, thus determining the methane solubility in the oil-based drilling fluid at the specified pressure, which will avoid the dissolution equilibrium shift caused by sampling compared with the liquid equilibrium sampling method.

An electric heater is used to heat the high-temperature thermal oil in the constant-temperature oil bath heating oven (26), with a heating power of 4,000 W, a maximum heating rate of 15° C./min, a temperature control range from room temperature to 150° C., and a temperature control accuracy of ±0.5° C. With the intelligent programmed high-prevision temperature control of the oil bath chamber, a constant temperature environment is enabled to make the pressure-resistant gas chamber (15) and the equilibrium still (25) immersed in the oil bath reach the target experimental temperature, with a fast heating rate and a high accuracy of temperature control and heat preservation, ensuring the safety and environmental protection of the whole determination process and improving the determination efficiency.

The gas booster pump (4) is used to pressurize the pressure-resistant gas chamber (15), taking compressed air as its driving air source with a driving air pressure range of 0.1 to 0.8 MPa, a driving flow rate range of 0.3 to 1 m³/min, an inlet pressure of 5 to 25 MPa and an outlet pressure of up to 160 MPa. With the gas booster pump (4), the methane in the high-pressure gas cylinder (1) is pressurized to the target experimental pressure and then injected into the pressure-resistant gas chamber (15), making the output pressure adjustable and controllable. The pressure-resistant gas chamber (15) and the equilibrium still (25) are internally equipped with a first precision inserted K-type thermocouple temperature sensor (13), a second temperature sensor (17), a first pressure sensor (14) with high-temperature compensation, and a second pressure sensor (24), with a temperature measurement accuracy of ±0.05° C. and a pressure measurement accuracy of 0.5% FS, which are used to monitor the temperature and pressure in the pressure-resistant gas chamber (15) and the equilibrium still (25). The pressure and temperature measurement signals are automatically collected and processed by the data acquisition system (31) and displayed on the panel of the computer (32), achieving accurate measurement of material temperature and pressure in the equilibrium still (25) and the pressure-resistant gas chamber (15). Considering the these three influencing factors (volume reduction of oil-based drilling fluid with increase in pressure, the volume change caused by rotation of hand high-pressure metering pump (23), and the volume occupied by pipes and valves), a set of methods to correct the volume of equilibrium still (25) occupied by methane when it reaches dissolution equilibrium in oil-based drilling fluid is proposed to avoid the influence of the three influencing factors on experimental results and improve the reliability of determination data.

Based on equal volume saturation method, the invention provides a device and method for determining the solubility of methane in oil-based drilling fluid at high temperature and pressure, which can determine the solubility of methane in oil-based drilling fluid at temperatures ranging from 30° C. to 150° C. and pressures ranging from 0 to 70 MPa, without sampling and analyzing the pressurized saturated drilling fluid, making the operation simpler, wherein a high-pressure dynamic seal structure and a high-pressure metering pump are used to displace hydraulic oil, technically solving the challenge that it is difficult to measure the gas solubility at a specified pressure with traditional constant-volume saturation method; furthermore, considering the volume compression of the drilling fluid under high pressure, the volume change caused by the rotation of high-pressure metering pump, and the volume occupied by pipes and valves, the volume $V_L$ of the oil-based drilling fluid can be easily obtained in combination with the known mass and density of the filled oil-based drilling fluid, and then used to correct the volume occupied by methane in the equilibrium still when it reaches dissolution equilibrium in oil-based drilling fluid to obtain reliable solubility determination data.

What is claimed is:

1. An experimental device for solubility determination of methane in oil-based drilling fluid comprises: a pressure-resistant gas chamber (15) and an equilibrium still (25) both arranged in a constant-temperature oil bath heating oven (26), and a gas booster pump (4) connected to the pressure-resistant gas chamber (15), wherein the gas booster pump (4) is connected to drive air source inlet (5), a gas check valve (10) is arranged on a pipe between the pressure-resistant gas chamber (15) and the gas booster pump (4), the gas booster pump (4) is also connected with a high-pressure gas cylinder (1), the equilibrium still (25) is divided into a dissolution equilibrium chamber at the top and a hydraulic oil chamber (27) at the bottom by a high-pressure dynamic seal structure (20), the dissolution equilibrium chamber is connected to a liquid inlet funnel (21) through the fourth globe valve (22), and the hydraulic oil chamber (27) is connected to a high-pressure metering pump (23) for replenishing hydraulic oil inside; wherein the experimental device further comprises a vacuum system (30) used for vacuuming the pressure-resistant gas chamber (15) and the equilibrium still (25);

wherein a first temperature sensor (13) and a first pressure sensor (14) are provided in the pressure-resistant gas chamber (15) for collecting temperature and pressure signals; a second temperature sensor (17) and a second pressure sensor (24) are provided in the dissolution equilibrium chamber for collecting temperature and pressure signals; the first temperature sensor (13), the first pressure sensor (14), the second temperature sensor (17), and the second pressure sensor (24) are connected to the data acquisition device (31).

2. The experimental device for solubility determination of methane in oil-based drilling fluid according to claim 1, wherein a gas filter (6), a first relief valve (7), a second pressure gauge (8) and an electric valve (9) are installed on the pipe between the air source inlet (5) and the gas booster pump (4).

3. The experimental device for solubility determination of methane in oil-based drilling fluid according to claim 1, the experimental device further comprises a first pressure gauge (2) for measuring the pressure of the high-pressure gas cylinder (1) and a first globe valve (3) for controlling its switch.

4. The experimental device for solubility determination of methane in oil-based drilling fluid according to claim 1, wherein the pipe between the pressure gas chamber (15) and the gas booster pump (4) is also provided with a second relief valve (11) and a second globe valve (12).

5. The experimental device for solubility determination of methane in oil-based drilling fluid according to claim 1, wherein an agitator blade (19) for agitation is set inside the dissolution equilibrium chamber, and is connected with an agitator motor (18).

6. The experimental device for solubility determination of methane in oil-based drilling fluid according to claim 1, wherein the vacuum system (30) is composed of a vacuum pump (29), with a fifth globe valve (28) set between the vacuum pump (29) and the equilibrium still (25), and a third globe valve (16) set between the pressure-resistant gas chamber (15) and the equilibrium still (25).

7. The experimental device for solubility determination of methane in oil-based drilling fluid according to claim 1, wherein the data acquisition device (31) is connected to a controller (32).

8. A method using the experimental device for solubility determination of methane in oil-based drilling fluid according to claim 1, comprising the following steps:

Step 1: Calibrate and verify the experimental device and pipe;

Step 2: Clean the equilibrium still (25), turn on the vacuum system (30) to vacuum, and test the air tightness of the experimental device;

Step 3: Heat the pressure-resistant gas chamber (15) and the equilibrium still (25) to the target temperature, turn on the vacuum system (30) for vacuuming, and inject the required drilling fluid into the dissolution equilibrium chamber in the equilibrium still (25) through the feed funnel (21);

Step 4: Fill a certain amount of methane into the pressure-resistant gas chamber (15), heat the pressure-resistant gas chamber (15) to the target temperature, and obtain the temperature $T_1$ and pressure $P_1$ of the methane in the pressure-resistant gas chamber (15) after the pressure is stabilized;

Step 5: Inject methane from the pressure-resistant gas chamber (15) into the dissolution equilibrium chamber of the equilibrium still (25) until it reaches the set pressure, and obtain the temperature $T_2$ and pressure $P_2$ as the gas is released from the pressure-resistant gas chamber (15) after the pressure is stabilized;

Step 6: Adjust the constant-temperature oil bath heating oven (26) to reach the required temperature, and observe the pressure change in the dissolution equilibrium chamber in real time; If the pressure decreases, inject hydraulic oil into the hydraulic oil chamber (27) through the high-pressure metering pump (23) until reaching the set pressure, and record $T_3$ and $P_3$ in the equilibrium still (25) after the pressure is stabilized;

Step 7: Calculate the solubility of methane in oil-based drilling fluid based on the measured parameters.

9. The method for solubility determination of methane in oil-based drilling fluid according to claim 8, wherein the solubility $R_S$ of methane in oil-based drilling fluid is calculated as follows:

$$n = \Delta n_g - n_{g3} = (n_{g1} - n_{g2}) - n_{g3}$$

Where, n is the mole fraction of methane dissolved in the oil-based drilling fluid; $n_{g3}$ is the mole number of methane in the equilibrium still (25) after the dissolution equilibrium is reached; $\Delta n_g$ is the mole number of methane released from the pressure-resistant gas chamber (15) into the equilibrium still (25); $n_{g1}$ is the mole number of methane in the pressure-resistant gas chamber (15) before it is released into the equilibrium still (25); $n_{g2}$ is the mole number of methane in the pressure-resistant gas chamber (15) after it is released into the equilibrium still (25);

The solubility $R_S$ is:

$$R_S = (n \times 22.4 \times 10^3)/V_L$$

Where, $V_L$ is the volume of oil-based drilling fluid at room temperature and atmospheric pressure.

10. The method for solubility determination of methane in oil-based drilling fluid according to claim 9, further comprising the correction of the mole fraction n of methane dissolved in oil-based drilling fluid as follows:

Step 1: Convert the mole fraction n of methane dissolved in oil-based drilling fluid is to the following formula:

$$n = \frac{V_{GC}(\rho_i - \rho_f)}{M_g} - (V_{EC} - V_L)\frac{\rho_g}{M_g} \quad (1)$$

Where, $V_{GC}$ is the volume of pressure-resistant gas chamber (15); $V_{EC}$ is the volume of equilibrium still (25); $V_L$ is the volume of oil-based drilling fluid added into the equilibrium still (25); $\rho_i$ is the density of methane in the pressure-resistant gas chamber (15) before it is released into the equilibrium still (25); $\rho_f$ is the density of methane in the pressure-resistant gas chamber (15) after it is released into the equilibrium still (25); $\rho_g$ is the molar density of methane in the equilibrium still after reaching dissolution equilibrium; $M_g$ is the molar mass of methane;

Step 2: Correct the influence of temperature and pressure on drilling fluid density;

$$\rho_2 = \rho_1/(1 + C_T \Delta T + C_P \Delta P) \quad (2)$$

Where, $\rho_1$ is the density of drilling fluid at room temperature and atmospheric pressure; $C_T$ is the coefficient of thermal expansion; $C_p$ is the coefficient of elastic compression; $\Delta T$ is the temperature difference between the measured target temperature and room temperature; $\Delta P$ is the pressure difference between the measured target pressure and atmospheric pressure;

Step 3: Correct the impact of temperature and pressure on the change of drilling fluid volume;

$$\Delta V = -\frac{\Delta \rho}{\rho}V_L = -\frac{\rho_2 - \rho_1}{\rho_1}V_L \quad (3)$$

Where, $\rho_2$ is the density of drilling fluid at the measured target temperature and pressure; $\rho_1$ is the density of drilling fluid at room temperature and atmospheric pressure; $V_L$ is the volume of oil-based drilling fluid at room temperature and atmospheric pressure; and $\Delta V$ is the volume change of drilling fluid caused by temperature and pressure changes;

Step 4: Correct the mole number n of methane dissolved in oil-based drilling fluid under high temperature and high pressure;

$$n = \frac{(V_{GC} + V_{pipe})(\rho_i - \rho_f)}{M_g} - [V_{EC} - (V_L + \Delta V) - V_{pump}]\frac{\rho_g}{M_g} \quad (4)$$

Where, $V_{pump}$ is the volume change caused by the filled hydraulic oil in the high-pressure metering pump (23), and $_eV_{pipe}$ is the volume occupied by the valve.

* * * * *